(12) United States Patent
Anderson et al.

(10) Patent No.: US 8,795,362 B2
(45) Date of Patent: *Aug. 5, 2014

(54) SUPPORT STRUCTURE IMPLANT FOR A BONE CAVITY

(75) Inventors: James Anderson, Leeds (GB); Ivan Green, Leeds (GB); Gary Moore, Leeds (GB)

(73) Assignee: Depuy International Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/203,063

(22) PCT Filed: Feb. 26, 2010

(86) PCT No.: PCT/GB2010/050332
§ 371 (c)(1),
(2), (4) Date: Aug. 24, 2011

(87) PCT Pub. No.: WO2010/097632
PCT Pub. Date: Sep. 2, 2010

(65) Prior Publication Data
US 2011/0313537 A1      Dec. 22, 2011

(30) Foreign Application Priority Data

Feb. 26, 2009  (GB) .................................. 09032475
Jul. 21, 2009  (GB) .................................. 09125980

(51) Int. Cl.
*A61F 2/28*           (2006.01)
(52) U.S. Cl.
USPC ..................................... 623/16.11; 623/17.11
(58) Field of Classification Search
USPC ................ 623/1.11, 1.22, 1.53, 16.11, 17.11, 623/17.12, 23.64, 23.69, 23.7; 606/63, 90, 606/105, 108, 113, 200
See application file for complete search history.

(56) References Cited

U.S. PATENT DOCUMENTS

| 4,770,725 | A  | 9/1988  | Simpson |
| 5,571,185 | A  | 11/1996 | Schug   |
| 5,972,015 | A  | 10/1999 | Scribner |
| 2004/0225296 | A1 | 11/2004 | Reiss |

(Continued)

FOREIGN PATENT DOCUMENTS

| DE | 4004472 A1      | 8/1991 |
| DE | 102007003645 A1 | 7/2008 |

(Continued)

OTHER PUBLICATIONS

UK Search Report GB0903247.5, date of search Jun. 17, 2009.

(Continued)

*Primary Examiner* — Bruce E Snow (57) ABSTRACT

A support structure implant for location within a bone cavity to support the bone which defines the cavity is formed from wires by braiding in a machine direction from a first end of the structure towards an opposite second end. The wires are formed into loops at the first end of the structure so that two lengths of wire extend away from each loop and a reformed into the braid. Each of the wires which is formed into the braid is held at the second end of the structure in a clamp. The clamp is provided by a support ring and a clamp ring which is formed from a shape memory alloy which can shrink to clamp the wires against the support ring when heated.

12 Claims, 5 Drawing Sheets

(56) References Cited

U.S. PATENT DOCUMENTS

| | | |
|---|---|---|
| 2005/0203508 A1 | 9/2005 | Thelen |
| 2005/0240193 A1 | 10/2005 | Layne |
| 2005/0261781 A1* | 11/2005 | Sennett et al. ............. 623/23.54 |
| 2006/0276887 A1* | 12/2006 | Brady et al. ................ 623/1.53 |
| 2007/0016163 A1 | 1/2007 | Santini |
| 2007/0043440 A1 | 2/2007 | William |
| 2007/0173939 A1 | 7/2007 | Kim |
| 2009/0149956 A1* | 6/2009 | Greenhalgh et al. ....... 623/17.11 |
| 2009/0182336 A1 | 7/2009 | Brenzel |
| 2011/0307021 A1 | 12/2011 | Anderson |
| 2011/0313537 A1 | 12/2011 | Anderson |

FOREIGN PATENT DOCUMENTS

| | | |
|---|---|---|
| EP | 1495729 A1 | 1/2005 |
| JP | 03-502898 A | 7/1991 |
| JP | 2004507274 A | 3/2004 |
| JP | 2004141301 A | 5/2004 |
| JP | 2009160399 A | 7/2009 |
| SU | 610330 A | 11/1985 |
| WO | WO 02056800 A2 | 7/2002 |
| WO | WO 2005102224 A2 | 11/2005 |
| WO | WO 2007131002 A2 | 11/2007 |
| WO | WO 2008099176 A1 | 8/2008 |
| WO | WO 2008099187 A2 | 8/2008 |
| WO | WO 2007078692 A3 | 12/2008 |
| WO | WO 2009012001 A1 | 1/2009 |
| WO | WO 2010097632 A1 | 9/2010 |
| WO | WO 2010097633 A1 | 9/2010 |
| WO | WO 2010097635 A1 | 9/2010 |
| WO | WO 2010097636 A1 | 9/2010 |

OTHER PUBLICATIONS

PCT International Search Report and Written Opinion PCT/GB2010/050332 dated Jun. 21, 2010.

Wang, Y. et al; Superelastic Cage Implantation; The Journal of Arthroplasty; Oct. 2009; pp. 1006-1014; vol. 24 No. 7; Elsevier Inc.

Schetky, L. M. Shape-Memory Alloys; Kirk-Othmer Encyclopedia of Chemical Technology. 2000; pp. 726 to 736; vol. 20; 2004 by John Wiley & Sons, Inc.

Duerig, T.W., et al; Engineering Aspects of Shape Memory Alloys; Butterworth-Heinemann (1990).

JP Office Action JP2011-551530, dated Dec. 3, 2013.

* cited by examiner

SUPPORT STRUCTURE IMPLANT FOR A BONE CAVITY

CROSS REFERENCE TO RELATED APPLICATION

This application is a National Stage 35 U.S.C. 371 of International Patent Application PCT/GB2010/050332 filed Feb. 26, 2010.

BACKGROUND OF THE INVENTION

This invention relates to a support structure implant which can be located within a bone cavity to support the bone which defines the cavity. It also relates to an assembly for deploying a stranded support structure implant in a bone cavity.

A cavity might be formed in a bone as a result of disease, or as a result of trauma, or as a result of a surgical procedure. Treatment of the condition can involve supporting the cavity while bone tissue regenerates within the cavity. A filler material can be provided in the cavity. This can be a curable material, for example an acrylate material similar to those used as bone cements to fix joint prosthesis components. It can be a material which stimulates regeneration of bone tissue, for example morcellised bone tissue.

Avascular necrosis (AVN), which is also known as osteonecrosis (ON), ischemic bone necrosis, or aseptic necrosis, results from the temporary or permanent loss of circulation to the bone tissue, and gives rise to localized death of the bone tissue. The loss of proper blood flow can result from trauma, or compromising conditions such as prolonged steroid use, alcohol use, gout diabetes, pancreatitis, venous occlusion, decompression disease, radiation therapy, chemotherapy, and Gaucher's disease.

Osteoporosis is an example of a condition in which bone tissue becomes weakened through a reduction in bone mineral density. Bone microarchitecture becomes disrupted, and the amount and variety of non-collagenous proteins in bone is altered. It can lead to collapse of vertebral structures. It can lead to hip fractures.

Conditions in which a bone is weakened can give rise to severe pain and limitation of movement within a short period, with a 70 to 80% chance of complete collapse of the bone, and of surrounding articulating surfaces when present, after only a few years if the condition is left untreated. In the case of avascular necrosis in the femoral head, it can be necessary for a patient to have joint replacement surgery. In the case of vertebral structures, it can be necessary for the structures to be reinforced to reduce the likelihood of collapse.

Treatments for AVN which focus on salvaging the head of the femur or other bone or joint include core decompression, osteomy, bone grafting, and vascularized fibular grafting.

Wang et al's paper entitled "Superelastic Cage Implantation: A New Technique for Treating Osteonecrosis of the Femoral Head with Middle-Term Follow-ups", published online in The Journal of Arthroplasty on 10 Oct. 2008, discloses a cage which is formed from 0.5 mm diameter wires. The wires are made from a nickel titanium alloy. The cage is formed from the wires by weaving wires manually. Loops of wire at the poles are held together by lacing a fine wire through the loops. The cage has a 4 mm diameter hole at each pole to allow bone chips to be positioned in the cage. The cage can be positioned in a femoral head through a bore in the femoral neck using an implantation tube.

BRIEF SUMMARY OF THE INVENTION

The present invention provides a cage for implantation in a bone cavity which is made from wires by a braiding process.

In one aspect, the invention provides a support structure implant for location within a bone cavity to support the bone which defines the cavity, in which the structure is formed from wires by braiding in a machine direction from a first end of the structure towards an opposite second end, and in which:

a. the wires are formed into loops at the first end of the structure so that two lengths of wire extend away from each loop and are formed into the braid, and b. each of the wires which is formed into the braid is held at the second end of the structure in a clamp.

The braided wires extend helically from the first end of the implant towards the opposite second end. Adjacent wires are wound in alternative senses, clockwise and anti-clockwise respectively, to form a tubular structure. Wires are interwoven as they extend helically around the implant at each crossing point. The implant is formed from an even number of wires. The transverse dimension of the tubular structure of the implant can be varied by varying the braid angle (which is the angle at which wires cross) along the length of the implant and the braid feed rate. The braid is formed from separate lengths of wire which extend to the second end so that the number of lengths of wire from which the braid is formed is equal to the number of free wire ends at the second end of the implant. Note however that each wire can be folded to form a loop at the first end of the implant so that the number of loops at the first end of the implant is equal to one half of the number of free ends at the second end of the implant.

In another aspect, the invention provides a support structure implant for location within a bone cavity to support the bone which defines the cavity, in which the structure is formed from wires by braiding in a machine direction from a first end of the structure towards an opposite second end, and in which each of the wires which is formed into the braid is held at the second end of the structure in a clamp which comprises a support and a shape memory alloy clamp ring which can clamp the wires between the ring and the support.

Forming the implant of the invention by braiding has the advantage that a throat can be formed at its second end conveniently by manipulating the braided structure to reduce its diameter. This can be more convenient with a braided structure than with a structure which is formed from wires using other techniques such as interweaving. A further advantage of the use of braiding is that the size of the implant can be changed conveniently by appropriate selection of the length of the braid.

It is a characteristic of a braid that the wires have free ends at the end of the implant towards which the braid is formed. The free ends of the braided structure must be restrained against unwrapping. This is in contrast to a structure which is formed by a technique such as weaving or knitting or knotting.

The implant of the invention can include a ring clamp at the second end to retain the wires in the throat portion, which includes an internal support ring. Preferably, the clamp includes a support ring and a clamp ring, and in which each of the wires is clamped between the support and clamp rings, especially with the support ring within the support structure and the wires clamped between the support ring and the clamp ring.

Preferably the ratio of (a) the distance between the internal support ring and the interface between the tapering portion and the throat portion to (b) the internal diameter of the throat portion is not more than about 1.0, more preferably not more than about 0.7, especially not more than about 0.5, for example not more than about 0.3 or not more than about 0.2 or in particular not more than about 0.1. Preferably, the distance between the internal support ring and the interface between the tapering portion and the throat portion is not more than about 10 mm, more preferably not more than about 5 mm, for example not more than about 0.3 mm. A support structure implant with a short throat portion is disclosed in the international patent application filed with the present application which claims priority from UK patent application no. 0903250.9.. Subject matter which is disclosed in the specification of that application is incorporated in the specification of the present application by this reference.

The implant of the present invention has the advantage that it can be made using conventional braiding equipment. This facilitates efficient manufacture of the implant of the present invention. It has the further advantage that the resulting implant can be made reproducibly so that its mechanical properties can be controlled. This can be important to ensure that appropriate support is provided to surrounding bone tissue when the support structure is implanted.

Each of the loops in the wires can be formed from two strands which are joined to form the loops. It can be preferred however that each of the loops in the wires is formed from a continuous looped strand. This has the advantage of ease of assembly and reliability. It can also help to reduce undesirable sharp points which might otherwise be provided by the ends of the wires.

Preferably, the implant includes a retainer for controlling the spacing between the loops at the first end of the implant. This can help to control the rigidity of the implant and its shape. The retainer can comprise a clip having a plurality of fingers which extend through the loops. For example, the clip can comprise a central hub and a plurality of fingers extending radially from the hub.

A retainer clip can provide one of a spigot and a socket. It can be used with an insertion tool which includes a probe end which carries the other of a spigot and a socket, so that the probe end and the clip can engage one another by means of the cooperating spigot and socket.

Accordingly, a retainer can have a socket formed in it which is aligned with the braiding axis. The socket will generally be open to the inside of the implant. The socket can extend through the retainer or it can be a blind opening in the form of a recess. A blind opening can be open on the face which faces the inside of the support structure. For example, the hub of a retainer clip can have a recess formed in it which is open to the inside of the implant.

When a retainer clip comprises a plurality of fingers, each of the fingers can be passed through at least one loop and folded back on itself. The folded finger can allow a loop in each such wire to pivot about the line on which the finger is folded, in a similar way to the flexing of a hinge. The extent of such movement of the wires relative to the retainer clip can vary around the clip, allowing asymmetric deformation of the implant prior to and during implantation, and when implanted. The clip can provide adequate control over the shape of the support structure during such implantation. For example, a clip can help to reduce the tendency for the implant to fold at the pole, instead ensuring that the shape of implant remains at least partly curved.

A retainer clip should be formed from a material which can withstand forces to which it is exposed during manufacture of the support structure implant, and during and after implantation. When the clip includes fingers which are folded, the material of the clip should be capable of being folded without breaking, and of retaining the folded shape. It will generally be preferred that the retainer clip be formed from a metal. Examples of suitable metals include certain stainless steels, for example such as are commonly used in the manufacture of implantable medical devices, especially clip devices.

A support structure implant which includes a retainer clip is disclosed in the international patent application filed with the present application which claims priority from UK patent application no. 0903249.1. Subject matter which is disclosed in the specification of that application is incorporated in the specification of the present application by this reference.

The support structure implant can flare outwardly from the first end. Preferably, the implant flares outwardly from the first end to a maximum transverse dimension at a wide point between the first and second ends and tapers inwardly between the wide point and the second end. Preferably, the shape of the implant is generally rounded when viewed from one side without any deforming forces. It will often be preferred that the implant is approximately circular when viewed in cross-section on a plane which is perpendicular to its axis. When the length of the implant is approximately equal to the diameter of the implant at its widest point, the support structure will be approximately spherical over most of its surface.

When the support structure implant flares outwardly from the first end, and it includes a retainer clip with fingers which extend through the wire loops, each finger can fit through two or more adjacent loops.

The support structure implant can be made by braiding wires over a form. Pins can be provided at the top of the form in an array which extends around the braiding axis. The loops in the braided wires can be formed by wrapping the wires around the pins. The pins will generally be spaced equidistantly around the form. The number of pins will generally be equal to one half of the number of wires which are braided to form the implant.

The shape of the form should be selected having regard to the desired shape of the support structure implant. For example, when the implant is required to have a generally rounded shape, the form will have a correspondingly rounded shape. The material of the wires and the processing of that material are selected so that the shape of the implant can be set by the application of heat. Heat treatments which can be used to set the shape of appropriately selected metallic materials will be known to appropriately skilled persons.

When the support structure implant flares outwardly from the first end to a maximum transverse dimension at a wide point between the first and second ends and tapers inwardly between the wide point and the second end, it can be formed in its intended shape using a combination of two or more forms. One form can be used to control the shape of the implant between one end and an adjacent wide point, and another form can be used to control the shape of the implant beyond that wide point.

For example, when the support structure implant has a constant diameter throat portion and a spherical portion, a first form can be used to create the part of the implant which includes the throat portion and one half of the spherical portion, and a second form can be used to create the other half of the spherical portion. The braided wires can be heat set over the first form before it is removed from within the wires and before the second form is placed within the wires. The braided wires can be heat set over the second form before it is removed from within the wires. The characteristics of the heat setting step will depend on the material of the wires. The heat setting step might involve, for example, annealing the material of the wires. When the wires are formed from a shape memory alloy, the characteristics of an appropriate heat setting step can be based on processes used to manufacture other products from such materials.

The apparatus for forming the support structure implant can be provided with features by which the wires can be held in place relative to the or each form. For example, a clamp can be used to fasten wires against a cylindrical form. Pins can be used to fasten looped ends of wires against a form.

The invention provides a method of making a stranded support structure implant for location within a bone cavity to support the bone which defines the cavity, which comprises:
 a. forming loops in a plurality of wires so that two lengths of each wire extend from each loop and capturing the loops,
 b. braiding the two lengths of each of the wires over a first form,
 c. heat setting the wires over the form,
 d. removing the form from within the wires.

In another aspect, the invention provides a method of making a stranded support structure implant for location within a bone cavity to support the bone which defines the cavity, which comprises:
 a. forming loops in a plurality of wires so that two lengths of each wire extend from each loop and fastening the loops against a support,
 b. braiding the two lengths of each of the wires to form the support structure having a first end provided by the loops in the wires and an opposite second end,
 c. clamping each of the wires at the second end of the support structure so as to retain the braided structure.

The loops can be captured using a set of pins, in which each loop is fitted around a respective one of the pins. The lengths of each wire should cross after the wire has passed around the pin. The lengths should cross symmetrically around the apparatus in the sense that each left hand length of a looped wire should pass over the right hand length, or alternatively each right hand length should pass over the left hand length.

The form can have a cylindrical portion and a flared portion. The method can include the step of clamping the two lengths of each of the wires on to the cylindrical portion of the form after the braiding step and before the heat setting step. The method can include a step of gathering the loops after the heat setting step. The gathering step will generally be preceded by a step of removing the first form. Preferably, the method includes a step of placing a second form within the braided wires after removing the first form. The second form can have a cylindrical portion and a spherical portion. The cylindrical portion of the second form can be fitted within the cylindrical portion of the braided wires resulting from the first heat setting step and clamped therein. The loops can then be gathered over the spherical portion of the second form. The gathered loops can be retained in place on the second form using pins which the loops can be fitted over. The loops can be provided on the surface of the spherical portion of the second form, preferably on the axis of the form. It can be preferred to fit more than two (or more) adjacent loops over each pin in order to form the tapered shape of the support structure implant.

In this technique for forming the support structure implant, the position of the braided wires between the cylindrical portion of the first form and the clamp determines the length of the braided wires which fits over the spherical portion of second form. The length of the wires between the clamp and the loops in the wires should be measured carefully so that the wires fit appropriately over the pins or another retainer for the looped wires.

The wires can be braided using commercially available braiding apparatus as used conventionally to form tubular articles from wire by braiding. The mechanical characteristics of the support structure can be controlled by varying the number of wires that are braided, and the braid angles, as is known.

The wires should be selected according to the desired mechanical properties of the support structure implant. Relevant variables include the material of the wires, the dimensions of the wires, the structure of the wires, and the processing of the wires.

Preferably, the wires are formed from a metal. Examples of suitable metals include certain stainless steels such as are commonly used in the manufacture of medical implants. It can be particularly preferred to use a shape memory alloy to form the wires of the support structure implant. Articles formed from shape memory alloys can exhibit shape memory properties associated with transformations between martensite and austenite phases of the alloys. These properties include thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase. It is possible to treat certain shape memory alloys so that they exhibit enhanced elastic properties. The enhanced elastic properties of shape memory alloys are well known in general, and are discussed in "Engineering Aspects of Shape Memory Alloys", by T W Duerig et al, Butterworth-Heinemann (1990). It is particularly preferred to use a shape memory alloy in the support structure of the present invention which has been treated so that it exhibits enhanced elastic properties. Examples of such alloys include nickel titanium based alloys, for example a nickel titanium binary alloy which contains 50.8 wt. % nickel. Techniques for treating a shape memory alloy so that it exhibits enhanced elastic properties, and to select desirable elastic properties, are known.

Each wire strand can be provided by a single filament. Each wire strand can be provided by a plurality of filaments. The use of wires provided by single filaments will generally be preferred because of the mechanical support characteristics that they can provide.

The number of loops will be equal to one half of the number of wires which are manipulated by the braiding machine to form the support structure implant. For example, the implant can be formed with 12 wires or 24 wires or 48 wires or 96 wires or 192 wires. The number of loops as the first ends of the support structure will then be 6, 12, 24, 48 and 96, respectively.

The transverse dimension of each wire strand (which will be its diameter when the wire has a circular cross-section) will generally be not more than about 1.0 mm, preferably not more than about 0.7 mm, for example about 0.5 or about 0.6 mm. The transverse dimension will generally be at least about 0.1 mm.

The support structure implant can have a throat portion at its second end, and include a ring clamp at its second end to retain the wires in the throat portion. The ring clamp can include an internal support ring. Preferably the ring clamp includes an outer ring, so that the wires can be fitted between the inner support ring and the outer ring. This can be achieved by use of an outer ring which can contract on to the inner support ring. The outer ring can include a mechanical arrangement by which it can be made to contract, for example in the form of a crimp. Preferably, the outer ring is formed from a shape memory alloy which has been treated so that it shrinks from a heat-unstable expanded configuration towards a heat-stable contracted configuration as the alloy reverts from its martensite phase to its austenite phase. Such behaviour of shape memory alloys is discussed in an article by L McDonald Schetky in the Encyclopedia of Chemical Technology (edited by Kirk-Othmer), volume 20 pages 726 to 736. Techniques for treating a shape memory alloy so that it exhibits thermally induced shape memory properties, and to select appropriate mechanical properties and transition temperatures for the alloy, are known.

It can be preferred to use a NiTiNb alloy such as disclosed in U.S. Pat. No. 4,770,725. Such alloys can be fabricated with transition temperatures in an appropriate range for a device which is to be implanted in a patient.

The transition temperatures of a shape memory alloy are affected by the composition of the alloy and the techniques which are used to process it. Preferably, the alloy is fabricated so that its characteristic $A_s$ and $A_f$ transition temperatures are 65° and 165° respectively. An alloy which has been treated in this way can maintain adequate clamping forces when exposed to temperatures in the range −60 to +300° C. The clamping forces can be released by exposing the alloy to a temperature which is less than −120° C.

In a further aspect, the invention provides a method of making a stranded support structure implant for location within a bone cavity to support the bone which defines the cavity, which comprises:
 a. braiding a plurality wires to form the support structure from a first end to an opposite second end,
 b. positioning the wires at the second end of the support structure between a support and a shape memory alloy clamp ring, and
 c. causing the shape memory alloy clamp ring to clamp the wires between the ring and the support so as to retain the braided structure.

The invention also provides an assembly which comprises the support structure implant of the invention and an insertion tool. The insertion tool can be used to place the support structure in the location in which it is to be implanted. It will usually be elongate. It will usually be relatively rigid. It can then be used to insert the support structure implant into a bone cavity through a bore in the bone that is prepared for this purpose.

The insertion tool can include (a) a probe end which can be used to engage a retainer clip at the first end of the implant, and (b) an engagement portion which can cooperate with engagement formations on the ring clamp. The probe end and the engagement portion can be moved relative to one another, in a direction which is aligned with the axis of the tool. The insertion tool can include an actuator which can cause relative movement between the probe end and the engagement portion. When the probe end is engaged with a retainer clip at the first end of the implant and the tool engagement portion is engaged with a clamp engagement portion at the second end of the implant, the actuator can be used to change the length of the implant and, as a consequence, its width. For example the actuator can be used to cause the length of the implant to increase and its width to decrease so that the implant can then be implanted in a patient through a bore which is formed in a bone. When the implant has been placed in its intended location, the actuator can be released so that the implant can recover towards its undeformed configuration and so that it can then provide a support for surrounding tissue.

An assembly of a support structure implant and an insertion tool is disclosed in the international patent application filed with the present application which claims priority from UK patent application no. 0903251.7. Subject matter which is disclosed in the specification of that application is incorporated in the specification of the present application by this reference.

In another arrangement, the implant might be fitted into a delivery device in which it is constrained for delivery through a bore in the patient's bone. The implant can be released from the delivery device and allowed to expand, towards the surfaces of the bone which defines a cavity in which the support structure is implanted. Such expansion can rely on the elasticity of the material of the implant, for example the enhanced elasticity that is available from certain shape memory alloys.

Preferably, the ring clamp has engagement formations by which the implant can be connected to an insertion tool. Examples of suitable engagement formations can include screw threads and a bayonet fitting. These and other suitable engagement arrangements are known from other implants and instruments for implanting them.

Preferably, the engagement formations are provided on an extension of the ring clamp, for example on an extension of the internal support ring. The extension will usually extend beyond the ends of the braided wires. Preferably, the extension and the internal support ring are formed from a single body of material, especially a metal, for example a stainless steel.

Preferably, a bore extends through the ring clamp, including any extension, so that material can be passed through it into the cavity within the implant. This can be used to place morcellised bone tissue within the cavity.

Preferably, the length of the throat portion of the support structure implant between the ring clamp and the portion of the structure which tapers toward the throat portion (which might be the polar extremity of a spherical portion) is short. This has the advantage that the throat portion can be supported against compression when a wider portion of the implant is deformed inwardly. For example, it can be preferred that the ratio of (a) the distance between the internal support ring and the interface between the tapering portion and the throat portion to (b) the diameter of the throat portion is not more than about 0.7, more preferably not more than about 0.5, especially not more than about 0.4, for example not more than about 0.3, in particular about 0.1.

Preferably, the distance between the internal support ring and the interface between the tapering portion and the throat portion is not more than about 10 mm, more preferably not more than about 7 mm, especially not more than about 5 mm.

The dimensions of the support structure implant can be varied when it is manufactured according to the size of the bone cavity in which it is to be implanted. When the implant is to be used in the treatment of a patient with AVN, for example in the femoral head, the cavity might have a transverse dimension (which approximates to a diameter of a spherical cavity) of 15 to 35 mm. Accordingly, the transverse dimension of the implant will preferably be at least about 15 mm, more preferably at least about 20 mm, especially at least about 30 mm. The transverse dimension of the implant will generally be not more than about 40 mm, preferably not more than about 35 mm. The implant should be a tight fit in the bone cavity, possibly so that it has some retained compression at least in some dimensions when implanted.

Factors affecting the appropriate transverse dimension of the throat portion of the implant can include the ability to pass material which stimulates regeneration of bone tissue (for example morcellised bone tissue) along its length, engagement between the implant and an insertion tool, and passage of the implant along a bore in a bone into the prepared bone cavity in which it is to be implanted. The internal transverse dimension of the throat portion defined by the braided wires is preferably not more than about 12 mm, more preferably not more than about 10 mm, for example not more than about 9 mm. The internal transverse dimension of the throat portion defined by the braided wires is preferably at least about 4 mm, more preferably at least about 6 mm, for example at least about 7 mm. The wall thickness of an internal support ring should be kept to a minimum, subject to it providing adequate support for the ring clamp, for example against compressive forces which are applied by means of an outer ring.

The implant can be implanted in a cavity within a bone to support the bone. The implant can be used to treat avascular necrosis, for example in the head of the femur. The implant can be used to treat degradation of vertebral structures, for example in the treatment of osteoporosis. The implant can be used to treat a bone structure which is weakened as a result of removal of tissue, for example in the treatment of a bone which has been affected by a tumour.

The support structure implant can be deployed within a cavity in a bone through a bore in the bone. The bore can be prepared using a drill or another cutting tool such as a reamer. When the implant is used in the treatment of AVN, for example in the femoral head, the bore can extend through the lateral femoral cortex and along the femoral neck. The bore can be straight for simplicity. It can be advantageous for the bore to be curved, in particular to locate the implant in the superior region of the femoral head. The bore will usually be circular in cross-section. Preferably, the diameter of the bore is at least about 3 mm, more preferably at least about 5 mm, for example at least about 7 mm. Preferably, the diameter of the bore is not more than about 20 mm, more preferably not more than about 15 mm, for example not more than about 10 mm.

An instrument for forming a curved bore in a bone for use in a surgical procedure to treat AVN is disclosed in US-A-2005/0203508 and WO-A-2008/099176.

Embodiments of the invention will now be described by way of example with reference to the accompanying drawings, in which.

BRIEF DESCRIPTION OF THE DRAWINGS

DETAILED DESCRIPTION OF THE INVENTION

Figure 1:
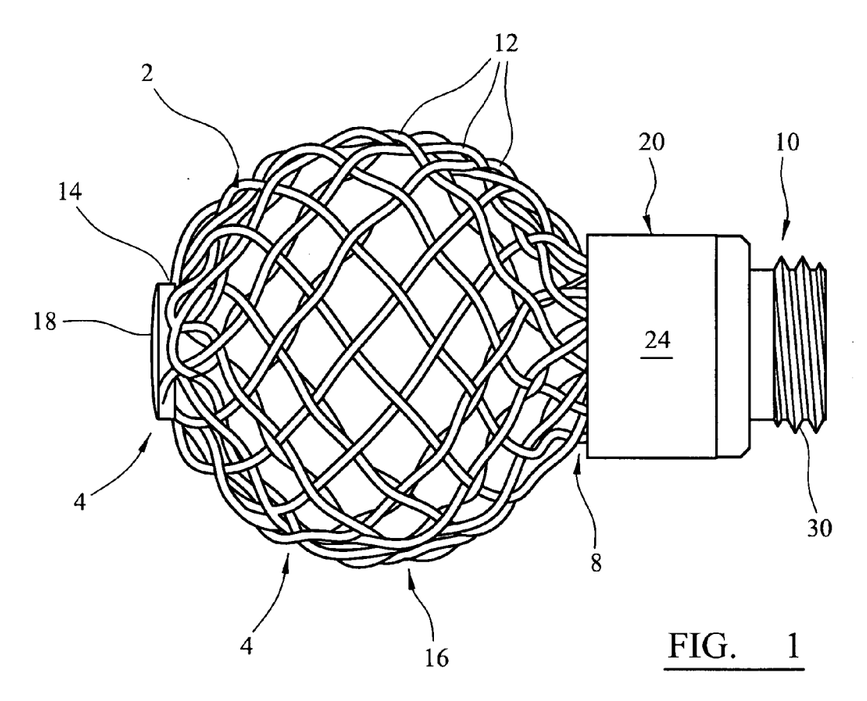
FIG. 1 is a side view of a stranded support structure implant for location within a bone cavity to support the bone which defines the cavity.

Referring to the drawings, FIG. 1 shows a stranded support structure implant 2 which can be implanted in a cavity in a bone, to support the bone which defines the cavity. The implant has a spherical portion 4 which is rounded at a first end 6 of the implant, and a cylindrical throat portion 8 at a second end 10 of the implant.

The implant 2 is formed from twelve wires 12 which are formed from a nickel titanium shape memory alloy which has been treated so that it exhibits enhanced elastic properties. The wires have a diameter of 0.5 mm.

Each of the wires is formed into a loop 14. The loops are gathered together at the first end 6 of the implant so that two lengths of each wire extend from the first end. There are therefore 24 lengths of the wires extending from the first end of the implant, which are braided. The configuration of the spherical portion 4 is such that the implant flares outwardly from the first end 6 towards a wide point 16, and tapers inwardly from the wide point towards the throat portion 8.

The implant includes a retainer clip 18 at its first end which engages the twelve loops 14 formed in the wires 12 to control their spacing. The retainer clip is described in more detail below with reference to FIG. 3.

Figure 2:
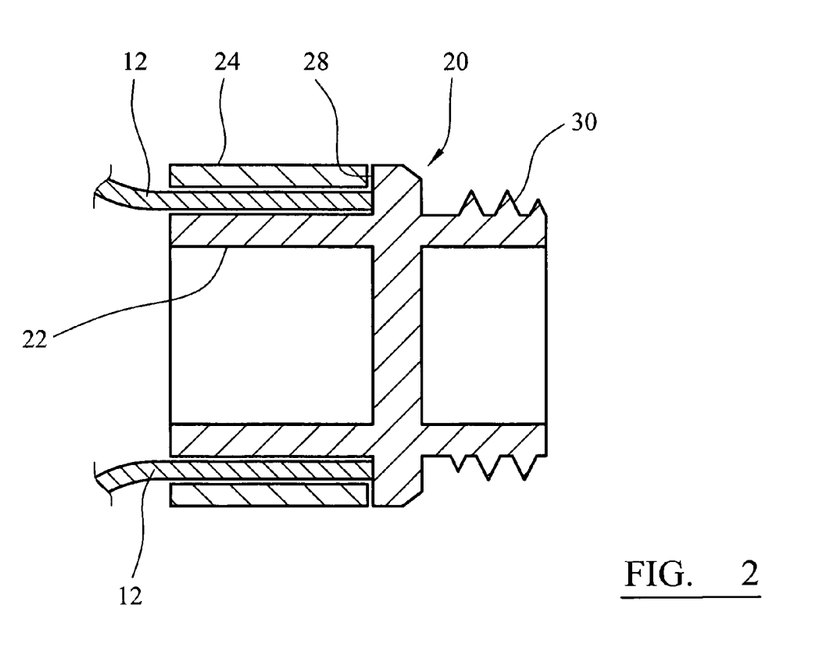
FIG. 2 is a sectional elevation through a part of the implant shown in FIG. 1, on the line II-II.

The implant includes a ring clamp 20. Details of the ring clamp are shown in FIG. 2. The ring clamp 20 comprises an internal support ring 22 and an outer ring 24. The internal support ring is formed from stainless steel. It defines a cylindrical support surface 26 which extends axially along the ring from a first end, up to a step 28. The internal support ring has an externally threaded collar 30 at its second end, beyond the step 28.

The outer ring 24 is formed from a nickel titanium based shape memory alloy which is treated so that it can be heated to a temperature which is above the characteristic $A_f$ temperature of the alloy to cause the ring to contract radially.

The ring clamp can be used to fasten the ends of the braided wires 12 at the second end of the device. The external diameter of the cylindrical support surface 26 of the internal support ring 22 is approximately equal to the internal diameter of the braided wires in the throat portion 8. The braided wires are trimmed to fit on the support surface 26, with their free ends abutting the step 28. The outer ring 24 is shrunk on to the wires so that they are clamped firmly between the outer ring and the support surface. The internal diameter of the outer ring if allowed to shrink without any restraint is slightly less than the external diameter of the wires when fitted over the cylindrical support surface of the internal support ring.

Figure 3:
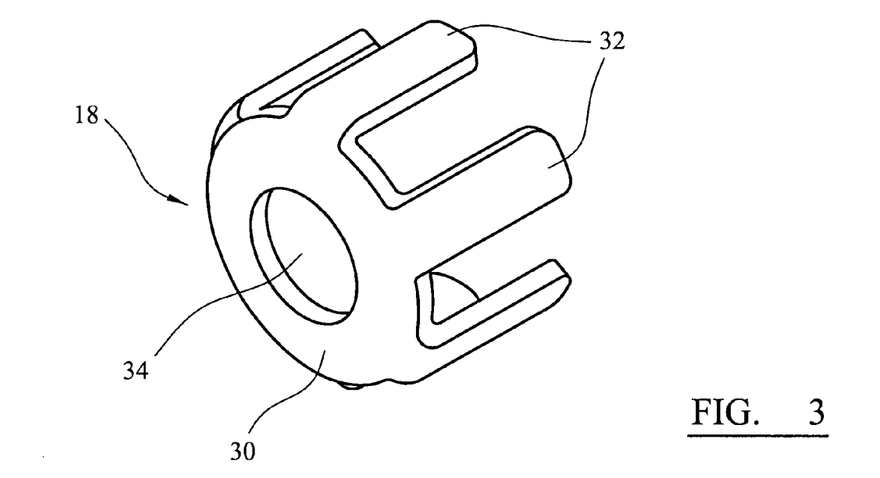
FIG. 3 is an isometric view from below of a retainer clip which can be used in the implant of the invention.

FIG. 3 shows the retainer clip 18 which is used at the first end of the support structure implant to retain the loops 14 in their gathered configuration. The clip comprises a central hub 30 and six fingers 32 which extend radially from the hub. The hub has a hole 34 extending through it. The clip is formed from stainless steel sheet by pressing.

Figure 4:
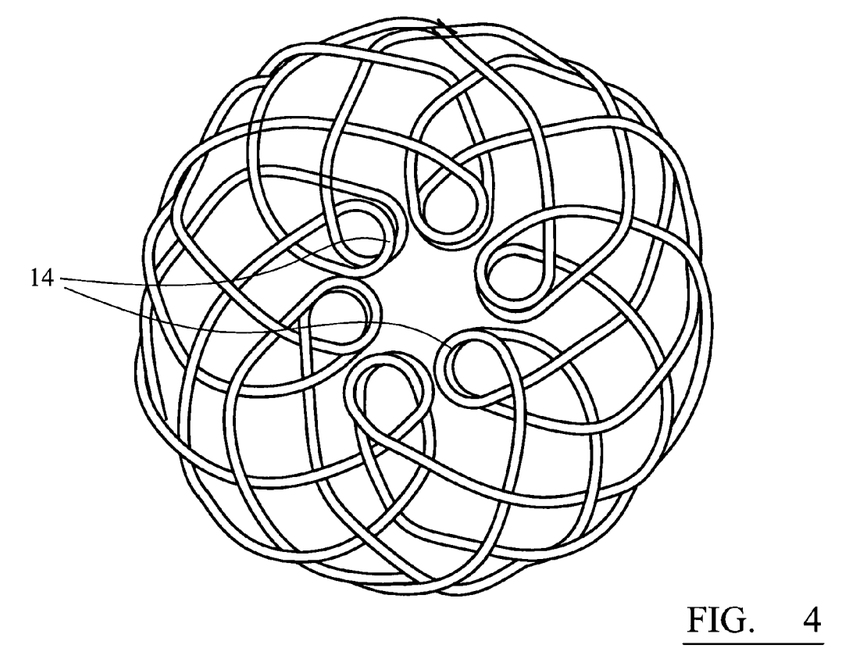
FIG. 4 is a top view of the stranded support structure implant showing its first end, with the retainer clip removed.

FIG. 4 shows the aligned loops 14 which are formed in the wires 12. As can be seen, the loops are aligned in pairs. Within each pair of aligned loops, one loop can be considered to be displaced in a clockwise direction relative to the other loop. On this basis, it can be seen in FIG. 4 that the clockwise loop of each pair is positioned under the anticlockwise loop. The reverse arrangement can be used in the alternative.

Each of the fingers 32 of the retainer clip 18 can be passed through two aligned loops 14 which are formed in the wires 12. Each finger can be folded back on itself and then retains its folded shape.

Use of the retainer clip at the first end of the implant means that, when the implant is subjected to a transverse compressive force, it tends to have a flatter, more rounded shape at the first end when subjected to a transverse compressive force compared with an implant which does not include a retainer clip, which tends to fold at the first end.

Figures 5A, 5B:
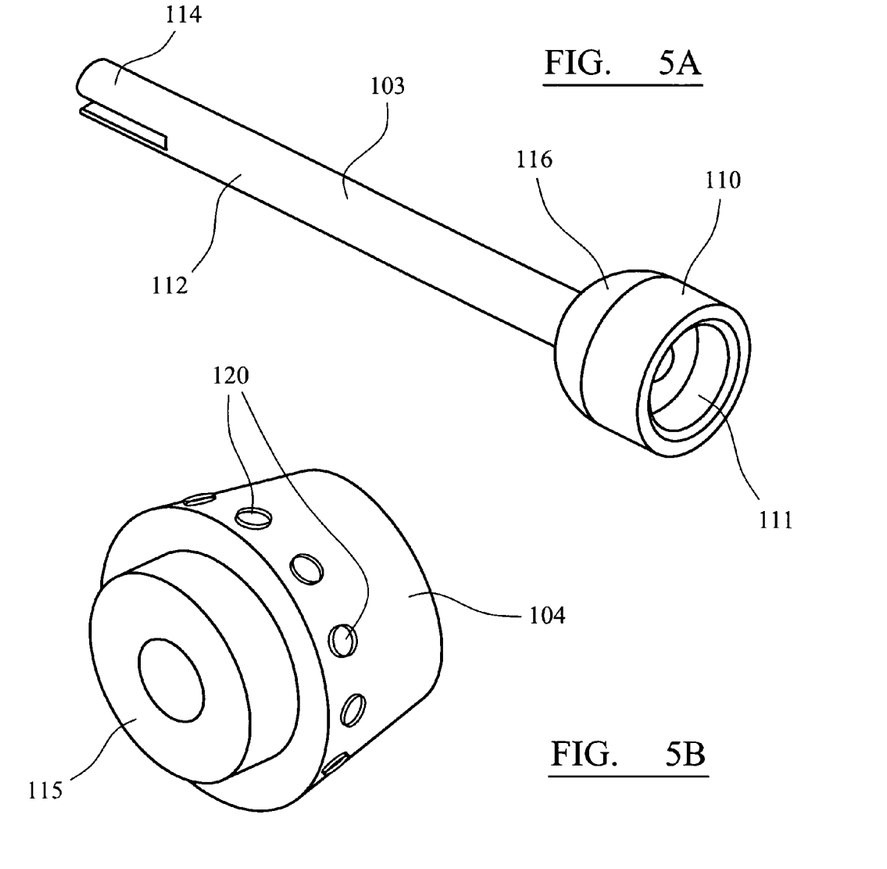
FIGS. 5a and 5b are isometric views of main and detachable parts of a first mandrel which can be used to make a braided support structure implant.
Figure 6:
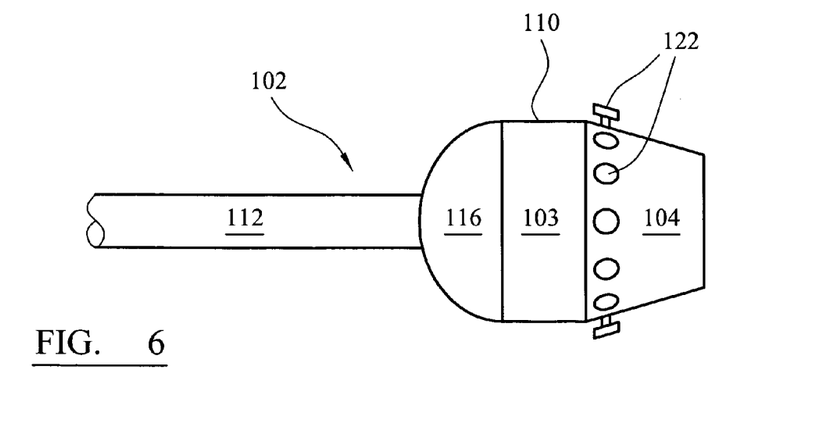
FIG. 6 is a side view of the first mandrel shown in FIG. 5.

FIGS. 5*a*, 5*b* and 6 show a first mandrel 102 which can be used in a braiding machine to in a first step of manufacturing a support structure implant according to the invention. The first mandrel has a main part 103 (FIG. 5*a*) and a detachable part 104 (FIG. 5*b*).

The main part 103 of the mandrel extends from a first end 106 to a second end 114. It has a constant diameter wide portion 110 at the first end, and a constant diameter narrow portion 112 at the second end 114. The mandrel includes a hemispherical transition portion 116 between the wide portion 110 and the narrow portion 112.

The main part of the mandrel has a blind socket 111 formed in it at the first end.

The detachable part 104 of the mandrel can be mounted end-to-end with the main part at the end of the wide portion 110. It has a spigot 115 which can fit in the socket 111 in the main part of the mandrel. Its diameter where it is mounted end-to-end with the wide portion is the same as that of the wide portion. The detachable part has a frustoconical shape, tapering inwardly in a direction away from the main part.

The detachable part 104 of the mandrel has twelve bores 120 formed in its on its outer cylindrical surface. The pins are spaced apart equally around the periphery of the mandrel, close to the wide portion of the main part of the mandrel. As shown in FIG. 6, a pin 122 can be fitted into each of the bores 120 Twelve lengths of wire are used in the braiding machine to fabricate the implant. In use, each length of wire is arranged so that it extends from one bobbin, around one of the pins on the mandrel, and back to another bobbin. Each wire is wound around a pin so that the two lengths of the wire cross between the pin and the bobbins. Each wire passes around its respective pin in the same direction (clockwise or anticlockwise).

The main part of the mandrel has a socket formed in it at the first end. The detachable part of the mandrel has a spigot formed on it. The main part and the detachable part can be fitted together by locating the spigot on the detachable part in the socket in the main part. Alternatively, the first mandrel can be made as a single component instead of having separable main and detachable parts. The first mandrel is shown ready for use in FIG. 6, with the spigot 115 on the detachable part 104 received in the socket 111 on the main part 103.

The dimensions of an embodiment of the first mandrel 102 are as follows:

| | |
|---|---|
| Diameter of narrow portion 112 | 7 mm |
| Radius of hemispherical portion 116 | 10 mm |
| Diameter of wide portion 110 | 20 mm |
| Length of wide portion 110 | 9.4 mm |
| Included angle of the frustoconical portion of detachable part 104 | 20° |
| Distance from wide portion to pins 122 | 2.5 mm |

Figure 7:
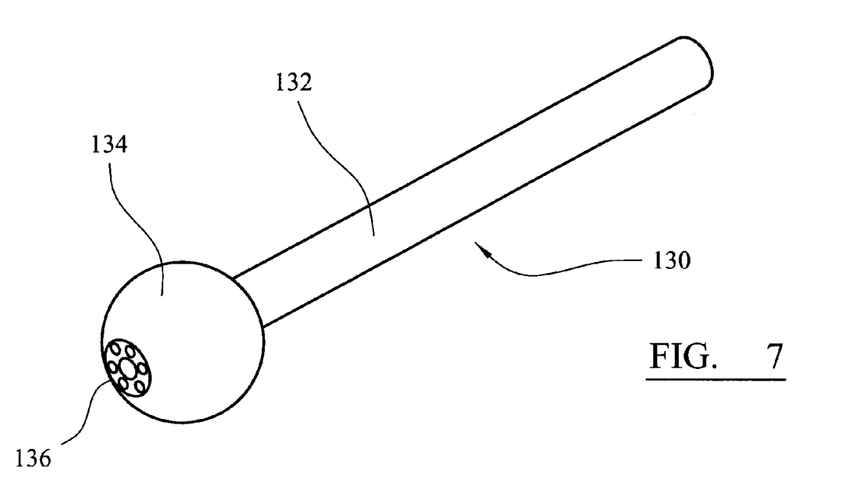
FIG. 7 is an isometric view of a second mandrel which can be used to make a braided support structure implant.

FIG. 7 shows a second mandrel 130. It has a constant diameter narrow portion narrow 132 which has the same dimensions as the constant diameter narrow portion 122 of the first mandrel. The constant diameter narrow portion is joined to a spherical portion 134. The diameter of the spherical portion of the second mandrel is the same as the diameter of the hemispherical transition portion 116 of the first mandrel. The second mandrel has six holes 136 at its first end which are spaced apart equally around the pole of the mandrel. Pins can be fitted into the holes.

A support structure implant according to the invention can be made from a wire made from a binary nickel titanium alloy containing 50.8 wt. % nickel. The alloy is treated so that the wire exhibits enhanced elastic properties at temperatures in the range 20 to 45° C.

The first mandrel is used in a braiding machine which has a plurality of bobbins with respective drives and mounts as used conventionally to form braided articles from wire. The braiding machine is operated conventionally to construct a tubular braid over the mandrel from the wires which are laid up between the bobbins and the pins, with each wire extending from a first bobbin, around a pin and back to a second bobbin.

The mandrel with the braided wires is removed from within the braiding machine after the wire has been braided over the wide portion 110, the hemispherical transition portion 116 and on to the narrow portion 112. First and second clamps are applied to the wires to clamp them to the narrow cylindrical portion 112. The first clamp is positioned as close as possible to the hemispherical transition portion 116. The second clamp is positioned so that the length of the braided tubular sleeve between the clamps is long enough to form the throat portion of the implant, and is not subject to any unravelling of the braid. The clamps should be capable of being tightened around the wires and the mandrel. Clamp designs might include for example hose clamps. A suitable clamp might make use of a screw thread actuator in the manner of a worm drive.

The first mandrel with the braided tubular sleeve is then placed in an oven at 500° C. for 15 minutes to heat set the wires so that they follow the shape of the mandrel.

Figure 8:
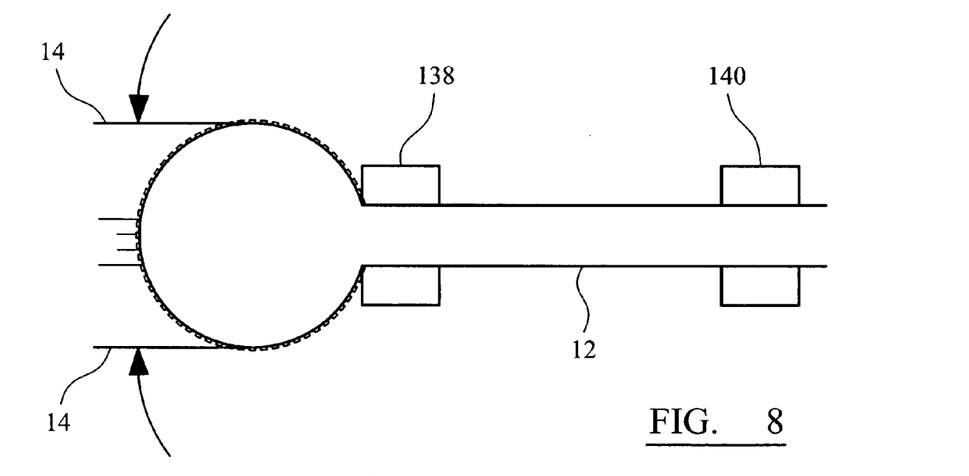
FIG. 8 shows the braided support structure implant positioned on the second mandrel during the manufacture of the implant.

The first and second clamps are then removed and the first mandrel 102 is removed from within the braided tubular sleeve. It is replaced with a second mandrel 130. As shown in FIG. 8, third and fourth clamps 138, 140 are fitted to the sleeve to clamp the wires to the narrow cylindrical portion 132. The third clamp is positioned as close as possible to the spherical transition portion 134. The fourth clamp is positioned so that the length of the braided tubular sleeve between the clamps is long enough to form the throat portion of the implant, and is not subject to any unravelling of the braid.

The distance between the holes 120 on the first mandrel for receiving pins and the transition between the hemispherical portion 116 and the constant diameter wide portion 110 of the first mandrel is the same as the distance measured on the spherical surface of the spherical portion 134 of the second mandrel between its equator and the holes 136 for receiving pins. Accordingly, the straight portion of the sleeve can be contracted around the spherical portion 134 of the mandrel and the loops 14 in the wires fitted over the holes 136 and held there by means of pins. Two loops are held in place by each pin. The mandrel with the braided tubular sleeve are then placed in an oven at 500° C. for 15 minutes to heat set the wires so that they follow the spherical shape of the second mandrel, and the second mandrel is then removed from within the sleeve.

The retainer clip is fitted at the first end of the braided sleeve, as discussed above with reference to FIG. 3.

A ring clamp 150 is fitted at the second end of the sleeve. The ring clamp is described above with reference to FIGS. 1 and 2. The braided wires are cut so that the length of the wires in the throat portion allows the cylindrical support surface 26 of the internal support ring 22 to fit within the throat portion with the wires sitting on the support surface, abutting the step 28. The outer ring 24 is shrunk on to the wires so that they are clamped firmly between the outer ring and the support surface. The internal diameter of the outer ring if allowed to shrink without any restraint is slightly less than the external diameter of the wires when fitted over the cylindrical support surface of the internal support ring.

The support structure implant can be implanted in a bone cavity to support the bone which defines the cavity, for example in the treatment of AVN in the femoral head.

A first step involves forming a tubular bore extending from the lateral cortex along the femoral neck, communicating with the affected region of the femoral head. This can be done with a bore cutting tool such as a drill.

A second step involves cutting away necrotic tissue. This can be achieved using a cutter which can be deployed in the vicinity of the necrotic tissue, such as those disclosed in US-A-2005/0240193 and WO-A-2008/0099187. The bone is then ready to receive the implant of the invention.

Figure 9:
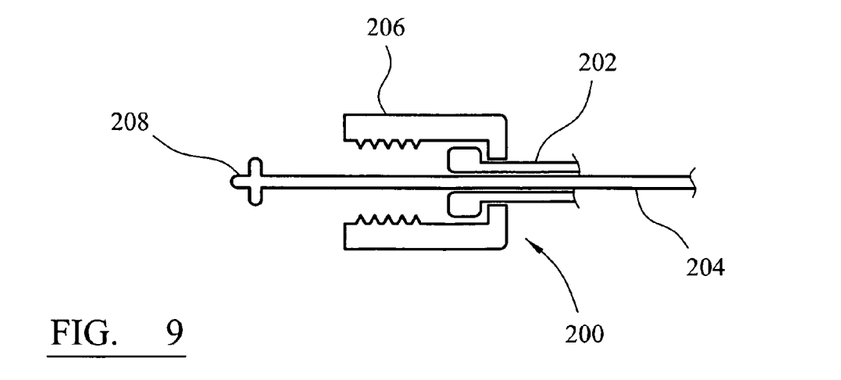
FIG. 9 shows an instrument which can be used to implant an implant.

FIG. 9 shows an insertion tool 200 can be used to implant which comprises an hollow sheath 202 having a shaft 204 arranged to slide within it. The sheath has a connector 206 at its remote end which is internally threaded so that it can engage the threads 30 on the internal support ring 22 of the ring clamp 20.

The shaft 204 has a tip 208 which can fit into the hole 34 in the hub 30 of the retainer clip 18.

Figure 10:
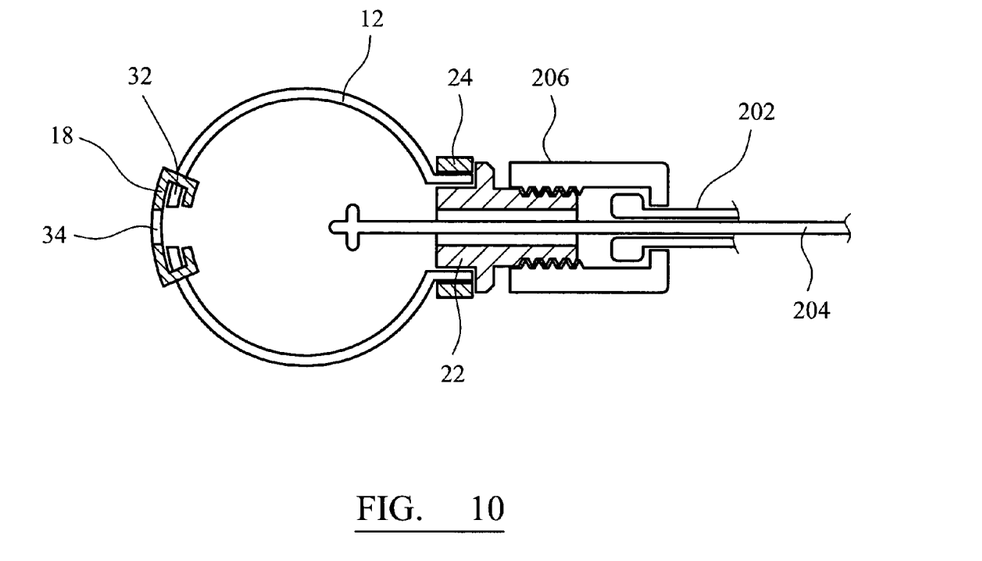
FIG. 10 shows the implant of the invention assembled on an instrument as shown in FIG. 9.

Accordingly, the support structure implant 2 can be fitted to the insertion tool 200 by inserting the tip 208 of shaft 204 through the throat of the implant and advancing sheath 202 is until the threads on the connector 206 can be engaged with the threads 30 on the internal support ring 22 of the ring clamp 20. FIG. 10 shows the implant and the insertion tool assembled in this way, with the wires 12 extending between the internal support ring 22 and the retainer clip 18 shown schematically.

The tip 208 of the shaft 204 can be advanced relative to the sheath 202 until it is received in the hole 34 in the hub of the retainer clip. Advancing the shaft 204 further relative to the sheath 202 causes the implant 2 to elongate and a consequent reduction in the width of the implant. In this way, by application of a force of, for example about 300 to 400 N, the length of the implant (measured from the end of the ring clamp to the first end of the implant) can be increased from 22 mm to about 30 mm, and its maximum width can be reduced from 22 mm to about 12 mm. The implant is shown in its elongated configuration in FIG. 11. Deformation of the implant in this way allows it to pass along a bore in the patient's bone, into the cavity in the bone. The folded fingers 32 of the clip allow the loops in each of the wires to pivot about the line on which the finger is folded, in a similar way to the flexing of a hinge. The extent of such movement of the wires relative to the retainer clip can vary around the clip, allowing asymmetric deformation of the implant prior to and during implantation, and when implanted. The clip can provide control over the shape of the support structure when it is deformed for such implantation. For example, a clip can help to reduce the tendency for the implant to fold at the pole, instead ensuring that the shape of implant remains at least partly curved.

Figure 11:
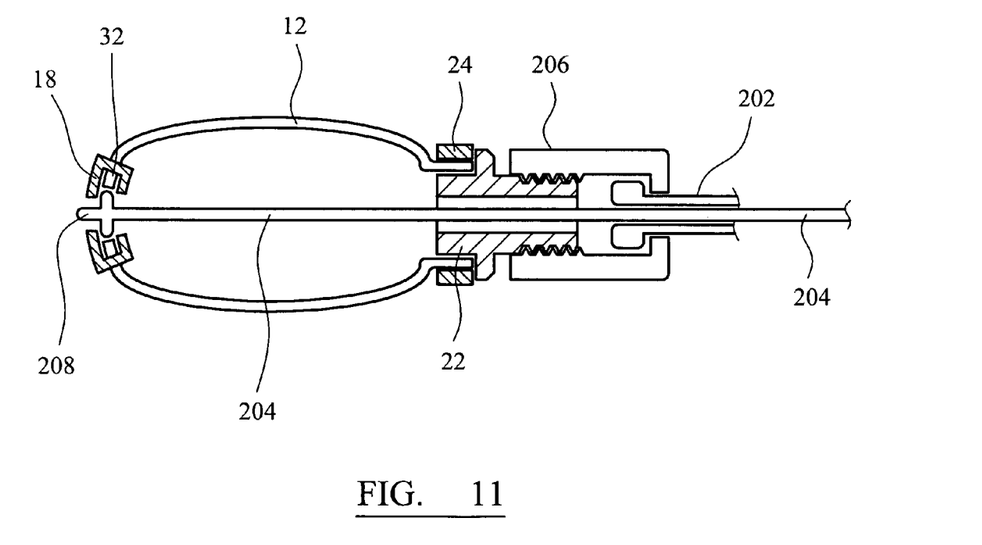
FIG. 11 shows the implant and instrument which are shown in FIG. 10, with the implant deformed for implantation by means of the instrument.

The insertion tool 200 can then be disengaged from the implant by unscrewing the threads on the connector 206 from the threads 30 on the internal support ring 22 of the ring clamp 20, and removed from within the patient's bone. Bone chips can then be placed within the cavity through the bore in the ring clamp and the throat portion of the implant.

It is an advantage of the implant of the invention that the screw threads on the ring clamp can be used to engage a tool, which might be similar to the insertion tool described above, in a procedure to remove the implant from within the bone cavity.

The invention claimed is:

1. An implant for location within a bone cavity, the implant comprising:
    a plurality of separate, interlaced wires that extend from a first end along a longitudinal axis to a second end, each of the wires having a first free end, a second free end and a loop, the loop being formed at the first end between the first free end and the second free end, the first free end and the second free end extending away from the loop toward the second end;
    a clamp comprising a support ring and an outer ring, the outer ring being spaced radially from the support ring, the support ring having an outer surface and the outer ring having an inner surface, and wherein the first free end and the second free end of each of the the plurality of wires is disposed between the outer surface of the support ring and the inner surface of the outer ring; and
    a clip having at least a first finger and a second finger, the first finger extending through the the first loop and the second finger extending through the second loop.

2. The implant of claim 1, wherein the loop of each of the plurality of wires is formed from a continuous looped strand.

3. The implant of claim 1, wherein the loop of each of the plurality wires is formed from two strands that are joined to form the loop.

4. The implant of claim 1, wherein the clip is configured to control the spacing between the first loop and the second loop.

5. The implant of claim 1, wherein the clip comprises a central hub and the first finger and the second finger extend radially from the hub.

6. The implant of claim 1, wherein the outer ring is formed from a shape memory alloy that has been treated so that the outer ring shrinks from a heat-unstable expanded configuration to a contracted configuration as a result of a change in phase of the alloy from martensite to austenite.

7. The implant of claim 1, wherein the outer surface of the support ring and the inner surface of the outer ring define an annular space within which the first free end and the second free end of the plurality of wires are disposed.

8. The implant of claim 4, wherein the plurality of wires are formed about a braiding axis.

9. The implant of claim 1, wherein each of the plurality of wires is formed from a metal.

10. The implant of claim 9, wherein each of the plurality of wires is formed from a shape memory alloy.

11. The implant of claim 1, wherein the plurality of wires form a structure having a spherical portion and a constant diameter portion, the constant diameter portion located at the second end.

12. The implant of claim 11, wherein the structure flares outwardly from the constant diameter portion to a maximum transverse dimension at a wide point between the first and second ends and tapers inwardly between the wide point and the second end.

* * * * *